US012576179B2

(12) United States Patent
    Awaji

(10) Patent No.:  US 12,576,179 B2
(45) Date of Patent:  Mar. 17, 2026

(54) VIRUS REMOVAL DEVICE

(71) Applicant: Clean Technology Co., Ltd., Osaka
    (JP)

(72) Inventor: Toshio Awaji, Osaka (JP)

(73) Assignee: CLEAN TECHNOLOGY CO., LTD.,
    Osaka (JP)

( * ) Notice: Subject to any disclaimer, the term of this
    patent is extended or adjusted under 35
    U.S.C. 154(b) by 401 days.

(21) Appl. No.: 18/030,835

(22) PCT Filed: Oct. 11, 2021

(86) PCT No.: PCT/JP2021/037531
    § 371 (c)(1),
    (2) Date: Apr. 7, 2023

(87) PCT Pub. No.: WO2022/080298
    PCT Pub. Date: Apr. 21, 2022

(65) Prior Publication Data
    US 2023/0302186 A1      Sep. 28, 2023

(30) Foreign Application Priority Data

Oct. 14, 2020  (JP) ................................. 2020-172918
    Nov. 10, 2020  (JP) ................................. 2020-187047
    Sep. 8, 2021  (JP) ................................. 2021-145869

(51) Int. Cl.
    *A61L 9/20*          (2006.01)
    *A61L 9/14*          (2006.01)
    *C02F 1/32*          (2023.01)
(52) U.S. Cl.
    CPC ................. *A61L 9/145* (2013.01); *A61L 9/20*
    (2013.01); *C02F 1/32* (2013.01); *A61L*
    *2209/12* (2013.01);
    (Continued)

(58) Field of Classification Search
    CPC ................................... A61L 9/145; A61L 9/20
    See application file for complete search history.

(56) References Cited

U.S. PATENT DOCUMENTS

2006/0273470 A1    12/2006  Takahashi et al.
2021/0178312 A1     6/2021  Awaji

FOREIGN PATENT DOCUMENTS

JP           6-327754          11/1994
JP         2000-210521          8/2000
            (Continued)

OTHER PUBLICATIONS

English Machine Translation of Awaji WO2019/116836 (Year: 2019).*

(Continued)

*Primary Examiner* — Donald R Spamer
(74) *Attorney, Agent, or Firm* — Wenderoth, Lind &
Ponack, L.L.P.

(57)                  ABSTRACT

A virus removal device providing a high virus removal probability, a small pressure loss of a flowing gas, and miniaturization with respect to an amount of air to be treated, by adopting a wet mechanism for removing a virus from a gas, the virus removal device includes a cylindrical treatment room to introduce a gas and remove a virus, a catcher formed of a rotary brush, installed in the treatment room and configured to collect the virus contained in the gas, a liquid spraying mechanism in the treatment room, a rotary driving mechanism to rotate the catcher, a gas introducing portion to introduce the gas to the treatment room, a gas discharging portion to discharge the gas from which the virus has been removed from the treatment room, and a liquid discharging portion to discharge a liquid containing the virus that has been removed from the gas.

5 Claims, 5 Drawing Sheets

(52) U.S. Cl.
CPC ..... *A61L 2209/134* (2013.01); *A61L 2209/15*
(2013.01); *C02F 2303/04* (2013.01)

(56) References Cited

FOREIGN PATENT DOCUMENTS

| | | |
|---|---|---|
| JP | 2006-334212 | 12/2006 |
| JP | 2011-10991 | 1/2011 |
| JP | 2015-171440 | 10/2015 |
| JP | 2020-96794 | 6/2020 |
| JP | 2020-151654 | 9/2020 |
| WO | 2019/116836 | 6/2019 |

OTHER PUBLICATIONS

English Machine Translation of Takahashi JP2006334212 (Year: 2006).*
International Search Report issued Dec. 28, 2021 in International (PCT) Application No. PCT/JP2021/037531.

* cited by examiner

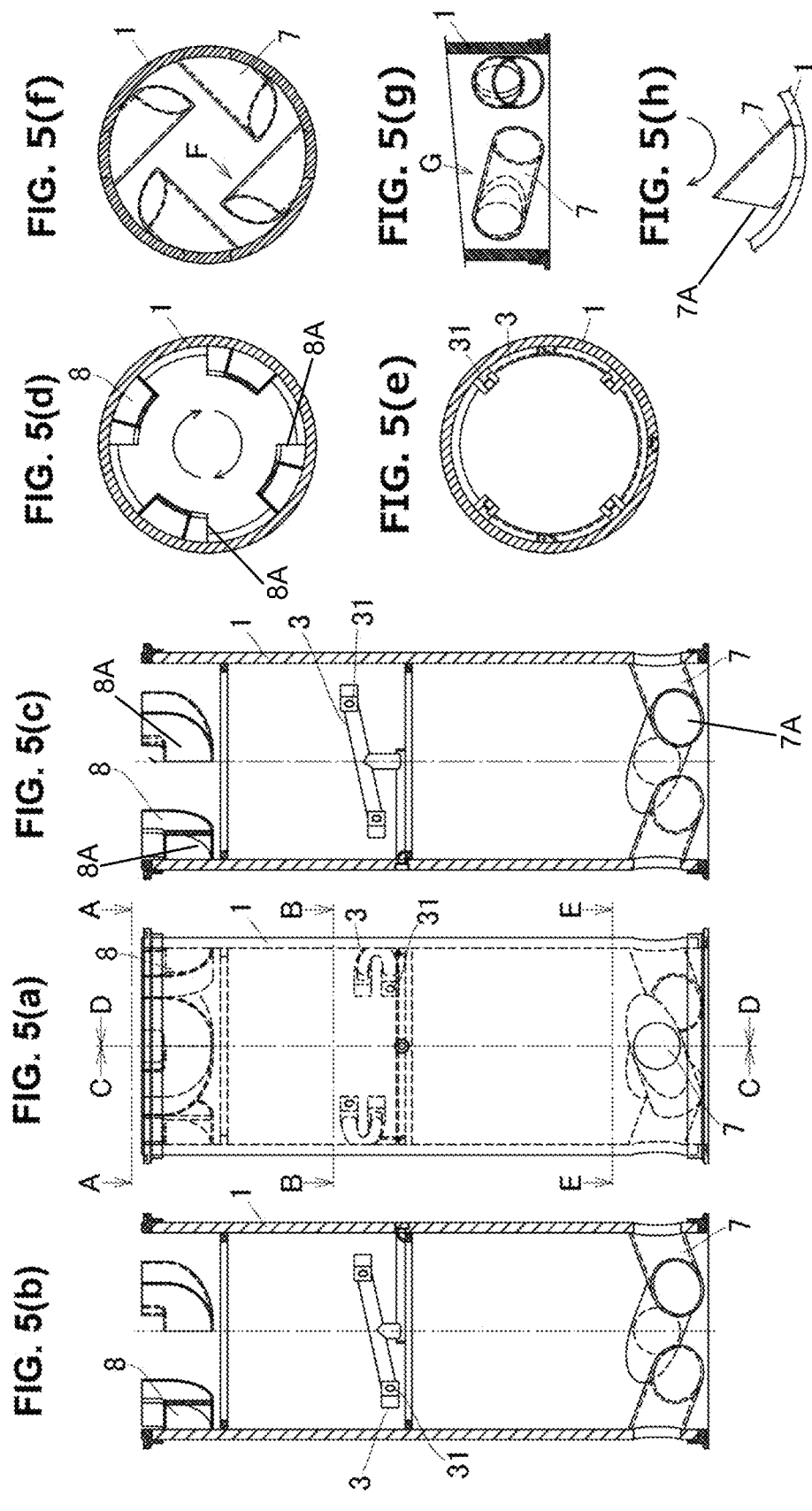

VIRUS REMOVAL DEVICE

TECHNICAL FIELD

The invention relates to a virus removal device for removing a virus from a gas.

BACKGROUND ART

Conventionally, as virus removal devices for killing or removing viruses, devices adopting various dry or wet mechanisms have been suggested (for example, see Patent Literatures 1 to 3).

Incidentally, among these conventional virus removal devices, devices adopting a wet mechanism such as the device disclosed in Patent Literature 3 are devices that kill or remove a virus by allowing a gas to pass through a filter on which a drug liquid has been sprayed. Therefore, although a high virus removal probability could be expected as compared to a dry mechanism, these devices had problems that the pressure loss of a gas that flowed in the device was high, and thus the device was made large with respect to an amount of air to be treated.

CITATION LIST

Patent Literatures

Patent Literature 1: JP 2011-10991 A
Patent Literature 2: JP 2020-151654 A
Patent Literature 3: JP 2020-96794 A

SUMMARY OF INVENTION

Technical Problem

In consideration of the problems of the invention which the above-mentioned conventional virus removal devices have, the present invention aims at providing a virus removal device that can achieve a high virus removal probability, gives a small pressure loss of the flowed gas, and can miniaturize the device with respect to an amount of air to be treated, by adopting a wet mechanism for removing a virus from a gas.

Solution to Problem

In order to attain the above-mentioned object, the virus removal device of the present invention is a virus removal device having a function to remove a virus from a gas, including: a cylindrical treatment room configured to introduce a gas and remove a virus from said gas; a catcher formed of a rotary brush, which is installed in said treatment room and configured to collect the virus contained in the gas; a liquid spraying mechanism installed in the treatment room; a rotary driving mechanism configured to rotate the catcher; a gas introducing portion configured to introduce the gas to the treatment room; a gas discharging portion configured to discharge the gas from which the virus has been removed from the treatment room, and a liquid discharging portion configured to discharge a liquid containing the virus that has been removed from the gas.

Here, the "virus" includes viruses such as coronaviruses, influenza viruses and noroviruses.

In this case, it is possible that the liquid spraying mechanism is installed in an intermediate position of the treatment room, and catchers formed of a rotary brush are disposed on both top and bottom sides of the liquid spraying mechanism.

Furthermore, it is possible to circulate the liquid that has been discharged from the liquid discharging portion into the liquid spraying mechanism.

Furthermore, it is possible that the liquid contains a component that kills the virus.

Furthermore, it is possible to include a light source configured to irradiate the liquid with a light that kills the virus.

Furthermore, it is possible that the gas is introduced from the gas introducing portion to the treatment room and the gas is discharged from the treatment room through the gas discharging portion by the action of only an airflow generated by rotation of the catchers formed of a rotary brush.

Advantageous Effect of Invention

According to the virus removal device of the present invention, by adopting a wet mechanism for removing a virus from a gas, a high virus removal probability can be achieved, and a pressure loss of a flowing gas is small, and the device can be miniaturized with respect to an amount of air to be treated.

Furthermore, by installing the liquid spraying mechanism in an intermediate position of the treatment room, and disposing catchers formed of a rotary brush on both top and bottom sides of the liquid spraying mechanism, the gas discharged from the discharging portion can be discharged in a dry state.

Furthermore, by configuring the device to circulate the liquid that has been discharged from the liquid discharging portion into the liquid spraying mechanism, the amount of the liquid used and the amount of discharged water can be reduced.

Furthermore, by incorporating a component that kills the virus in the liquid, it is possible to kill a virus contained in a gas to be treated and a virus contained in the liquid.

Furthermore, by including a light source configured to irradiate the liquid with a light that kills the virus, it is possible to kill a virus contained in a gas to be treated and a virus contained in the liquid.

Furthermore, by introducing the gas from the gas introducing portion to the treatment room and discharging the gas from the treatment room through the gas discharging portion by an action of only an airflow generated by rotation of the catchers formed of a rotary brush, it is possible to configure the virus removal device that has been independently installed to act only by a driving force of the rotary driving mechanism configured to rotate the catcher to thereby make the configuration of the device simple, and it is also possible to easily achieve a balance between a flow amount (treatment amount) of the gas and a virus remove ability.

BRIEF DESCRIPTION OF DRAWINGS

FIGS. 5 (*a*)-5 (*h*) are explanatory drawings illustrating the fourth modified example of the virus removal device of the present invention, in which FIG. 5 (*a*) is an overall elevational view, FIG. 5 (*b*) is a C-C cross-sectional view of FIG. 5 (*a*), FIG. 5 (*c*) is a D-D cross-sectional view of FIG. 5 (*a*), FIG. 5 (*d*) is an A-A arrow view of FIG. 5 (*a*), FIG. 5 (*e*) is a B-B cross-sectional view of FIG. 5 (*a*), FIG. 5 (*f*) is an E-E cross-sectional view of FIG. 5 (*a*), FIG. 5 (*g*) is an F arrow view of FIG. 5 (*f*), and FIG. 5 (*h*) is a G arrow view of FIG. 5 (*g*).

DETAILED DESCRIPTION OF PREFERRED EMBODIMENTS

Hereinafter the embodiments of the virus removal device of the present invention will be explained based on the drawings.

Figure 1:
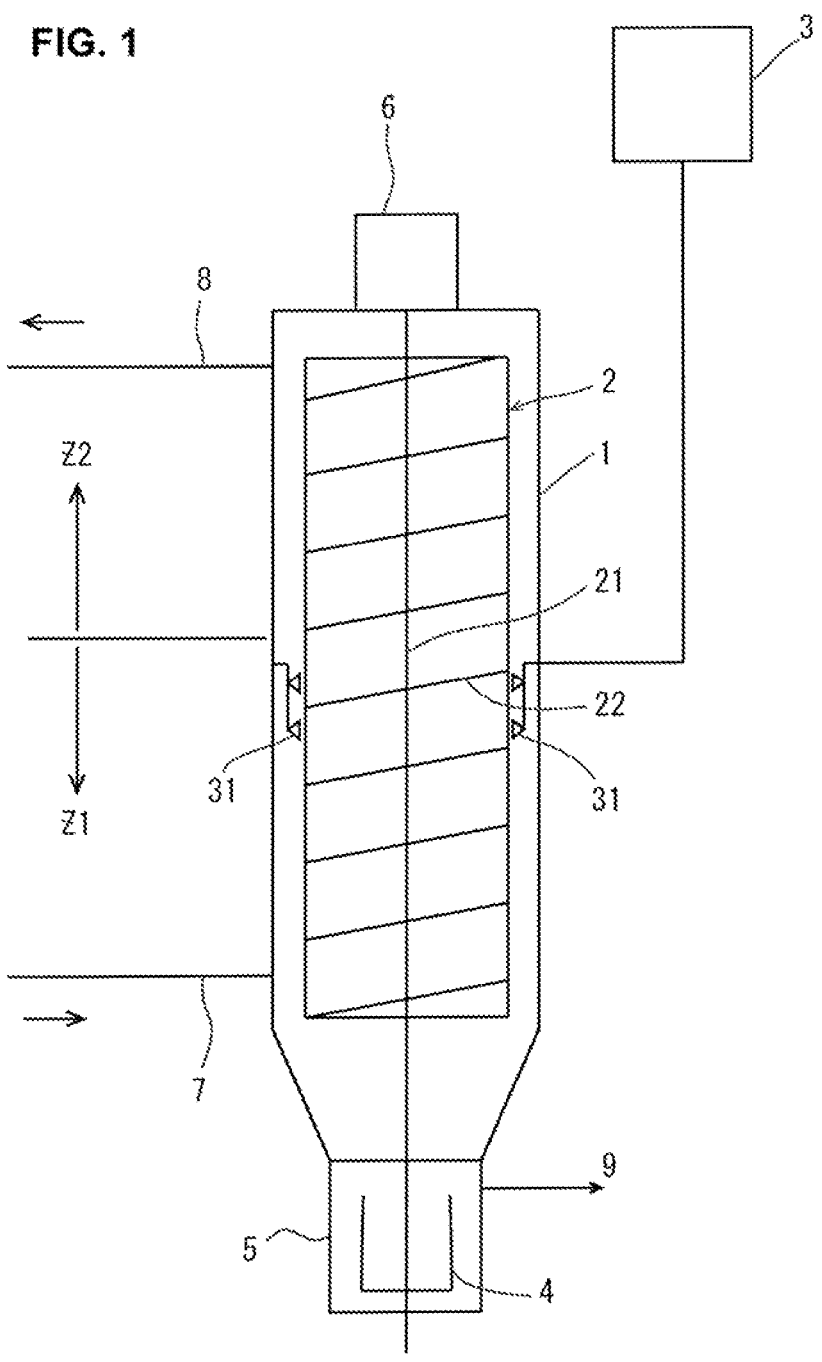
FIG. 1 is an explanatory drawing illustrating an example of the virus removal device of the present invention.
Figure 2A:
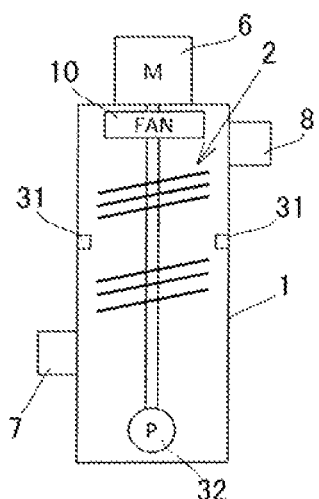
FIGS. 2 (a)-2 (d) are explanatory drawings illustrating the first modified example of the virus removal device of the present invention.
Figure 2B:
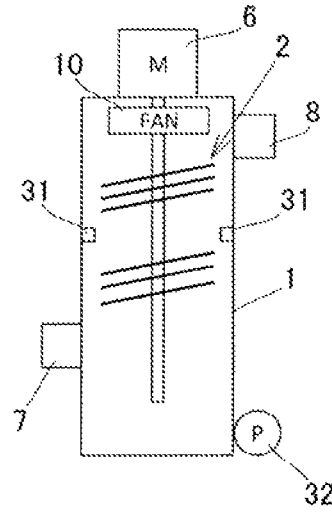
Figure 2C:
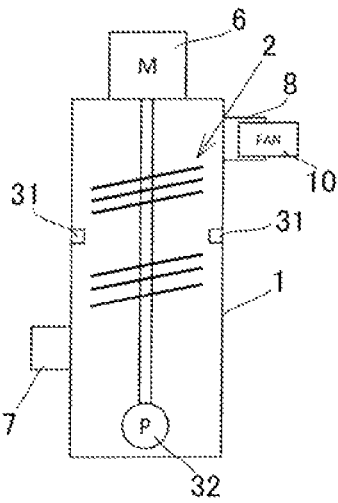
Figure 2D:
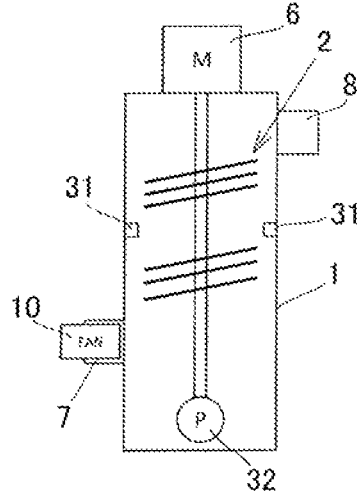

FIG. 1 illustrates an example of the virus removal device of the present invention.

This virus removal device is for removing a virus from a gas, and includes a tubular, preferably cylindrical treatment room 1 configured to introduce a gas and remove a virus from this gas, a catcher 2 formed of a rotary brush including a support 21 and hair 22 planted thereon, which is installed in the treatment room 1 and configured to collect the virus contained in the gas, a liquid spraying mechanism 3 installed in the treatment room 1, a liquid storage portion 5 equipped with a stirrer 4 formed on the bottom of the treatment room 1, a rotary driving mechanism 6 configured to rotate the catcher 2 and the stirrer 4, a gas introducing portion 7 configured to introduce the gas into the treatment room 1, a gas discharging portion 8 configured to discharge the gas from which virus has been removed from the treatment room 1, and a liquid discharging portion 9 configured to discharge a liquid containing the virus that has been removed from the gas.

Here, the "virus" includes viruses such as coronaviruses, influenza viruses and noroviruses.

Examples of the brush including the support 21 and the hair 22 planted thereon, which constitutes the catcher 2, include a brush including the support 21 and the hair 22 planted on a local part of the support 21 and a brush including the support 21 and the hair 22 planted by dispersing over almost all of the support 21.

Examples of the brush including the support 21 and the hair 22 provided with focusing on a local part of the support 21 include a spiral brush (the present example), a disk brush, etc.

It is preferable that the brush constituting the catcher 2 is configured so that the tip of the hair 22 planted on the support 21 is brought into contact with the inner periphery surface of the cylindrical treatment room 1.

By this way, the inner periphery surface of the treatment room 1 can always be maintained in a clean state by the brush constituting the catcher 2.

The materials for the support 21 and the hair 22 of the brush are not particularly limited, but considering the treatment temperature, in the cases where the treatment temperature is relatively low, such as ordinary temperature or room temperature to about a hundred and tens ° C., various types of synthetic resins such as polyethylene terephthalate resins and polyamide resins, which have relatively low heat resistance, and conductive synthetic resins formed by incorporating a powder of a fine conductor such as a metal or carbon in these synthetic resins, etc. can be used. In the cases where the treatment temperature is higher than this temperature, synthetic resins having high heat resistance, highly heat-resistant conductive synthetic resins formed by incorporating a powder of a fine conductor such as a metal or carbon in these high heat resistant synthetic resins, and metals are used. In the cases where the treatment temperature is raised, the heat in the treatment room can be efficiently absorbed by the catcher by selecting materials especially high in heat conductivity such as metals such as copper, aluminum, iron and stainless steel or ceramic wool, or fibers formed by a mixture of a metal and a ceramic. Furthermore, in the case where a heating means for heating this catcher is provided, the generated heat of the heating means can be efficiently transferred to the surface of the catcher. By this way, the treating capacity of the apparatus during starting can be rapidly increased and the treatment to kill the virus on the surface of the catcher can be advanced.

The liquid spraying mechanism 3 installed in the treatment room 1 has a nozzle 31 for spraying the liquid, which is installed on an intermediate position of the treatment room 1.

In this case, it is preferable to constitute the hair of the catcher 2 formed of the brush at the upper side position Z2 from the position where the nozzle 31 is installed by a material such as a polyolefin resin such as a polypropylene resin, a synthetic resin such as a polyethylene terephthalate resin, or a hydrophobic (water repellant) material such as a metal.

Furthermore, the hair of the catcher 2 formed of the brush at the lower position Z1 that is lower than the position where the nozzle 31 is installed can be constituted with the same material as this, or a hydrophilic material such as a polyamide resin nylon, a polyvinyl chloride resin or a polyvinylidene chloride resin.

By this way, by brushing off the liquid by the catcher 2 formed of a brush with hair constituted by a hydrophobic (water repellant) material at the position Z2 which is higher than the position where the nozzle 31 of the liquid spraying mechanism 3 is installed, the gas discharged from the gas discharging portion 8 can be discharged in a dry state.

Furthermore, by capturing the virus by tangling it with the catcher 2 formed of a brush with hair constituted by a hydrophilic material at the position Z1 which is lower than the position where the nozzle 31 of the liquid spraying mechanism 3 is installed, the virus removal efficiency can be improved.

The position for installing the nozzle 31 is not limited to the intermediate position in the treatment room 1 of the present example, and the nozzle 31 can be installed on the upper position of the treatment room 1, or on the support 21 of the brush constituting the catcher 2.

The liquid to be sprayed from the liquid spraying mechanism 3 can contain, besides water (or hot water), a component that can kill the virus contained in air to be treated or the virus contained in the liquid.

Examples of this component (drug liquid) can include an aqueous sodium hypochlorite solution, aqueous hypochlorous acid, surfactants (sodium straight chain alkyl benzenesulfonates, alkyl glycosides, alkylamine oxides, benzalkonium chloride, benzethonium chloride, dialkyldimethylammonium chlorides, polyoxyethylene alkyl ethers, pure soap components (potassium aliphatic acids, sodium aliphatic acids), etc.), ozone (water), photocatalyst substances such as titanium dioxide, etc.

For these components (drug liquids), said components (drug liquids) can be directly introduced from a feeding device (illustration is omitted) to the virus removal device, or the generating device can be incorporated in the virus removal device.

Furthermore, the virus can be killed by installing a light source (illustration is omitted) that generates a light that kills the virus such as an ultraviolet ray, a deep ultraviolet ray (excimer laser beam) or an infrared ray (including those aiming at generating ozone (water) or interaction with a photocatalyst substance) in the treatment room 1 or a liquid flow path such as the liquid storage portion 5 formed on the bottom of the treatment room 1.

The liquid storage portion 5 equipped with the stirrer 4 formed on the bottom of the treatment room 1 once collects and stores the liquid containing the virus that has been collected by the catcher 2 and washed off by the liquid sprayed from the spray mechanism 3, and sequentially discharge the liquid via the liquid discharging portion 9.

Here, the shape of the stirrer 4 is not specifically limited as long as it can discharge the liquid containing the virus stored in the virus storage portion 5 in a stirred state, and a stirrer having a rod shape, or a stirrer having a screw shape or a propeller shape, etc. can be adopted.

By this way, the liquid containing the virus can be smoothly discharged in a homogenized state.

The stirrer 4 can be omitted depending on the characteristic of the gas to be treated or the content of the treatment.

The liquid storage portion 5 can be integrally formed on the bottom of the treatment room 1, or can be detachably installed in the treatment room 1 for maintenance or a treatment of a large amount of virus.

The rotary driving mechanism 6 for rotating the catcher 2 and stirrer 4 are for rotating the catcher 2 and stirrer 4 so as to enhance the collecting effect of the virus by the catcher 2 and the effect of homogenizing of the liquid containing the virus stored in the liquid storage portion 5 by means of the stirrer 4.

Incidentally, although the rotating shaft of the catcher 2 (brush support 21) and the rotating shaft of the stirrer 4 are constituted by the same shaft and the rotary driving mechanism 6 is set as a common rotary driving mechanism in this example, individual driving mechanisms can also be adopted.

Furthermore, for the rotating shaft (brush support 21) of the catcher 2 and that of the stirrer 4, bearings are provided to both ends so that high-speed rotation of 1000 rpm, for example, is made possible, but it is possible to provide a bearing only at the upper end.

Here, the number of revolutions of the rotation axis of the catcher 2 is preset to about 100 to 3, 600 rpm, preferably 300 to 2,400 rpm, more preferably 600 to 1,800 rpm, with consideration for the effect of collecting virus by the catcher 2, consumed energy, etc.

Furthermore, by circulating the liquid that has been collected in the liquid storage portion 5 to the liquid spraying mechanism 3, the use amount and discharge amount of the liquid can be reduced.

In this case, the liquid circulating passage (illustration is omitted) can be provided, as necessary, with a filter, a pump, a selector valve, etc.

Specifically, in the virus removal device equipped with the treatment room 1 having a diameter of 200 mm, the liquid of several L/min to hundreds of L/min, preferably tens of L/min is normally sprayed from the liquid spraying mechanism 3, but through the circulated use of the liquid, the liquid consumption and discharge quantity can be reduced to ¹⁄₁₀ or less of the liquid sprayed.

Incidentally, the virus removal device of the present example can be installed by allowing the device to mediate in midstream of a duct in which the gas is flowed, or can be independently installed.

In this case, as shown in the first modified example illustrated in FIG. 2, a pump 32 for circulating the liquid, and a fan 10 for flowing the gas can be installed.

Figure 3C:
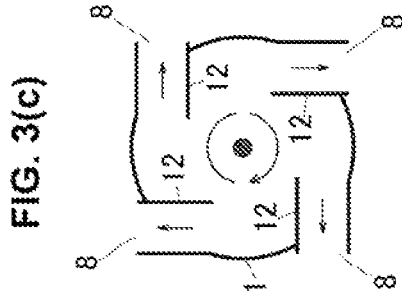
FIGS. 3 (a)-3 (c) are explanatory drawings illustrating the second modified example of the virus removal device of the present invention, in which FIG. 3 (a) is an overall elevational view, FIG. 3 (b) is an X-X cross-sectional view of FIG. 3 (a), and FIG. 3 (c) is a Y-Y cross-sectional view of FIG. 3 (a).
Figure 3B:
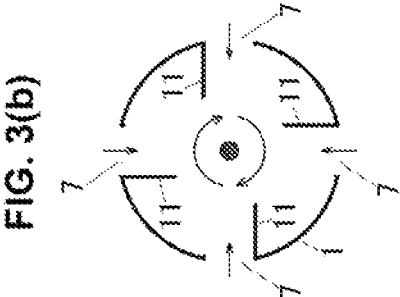
Figure 3A:
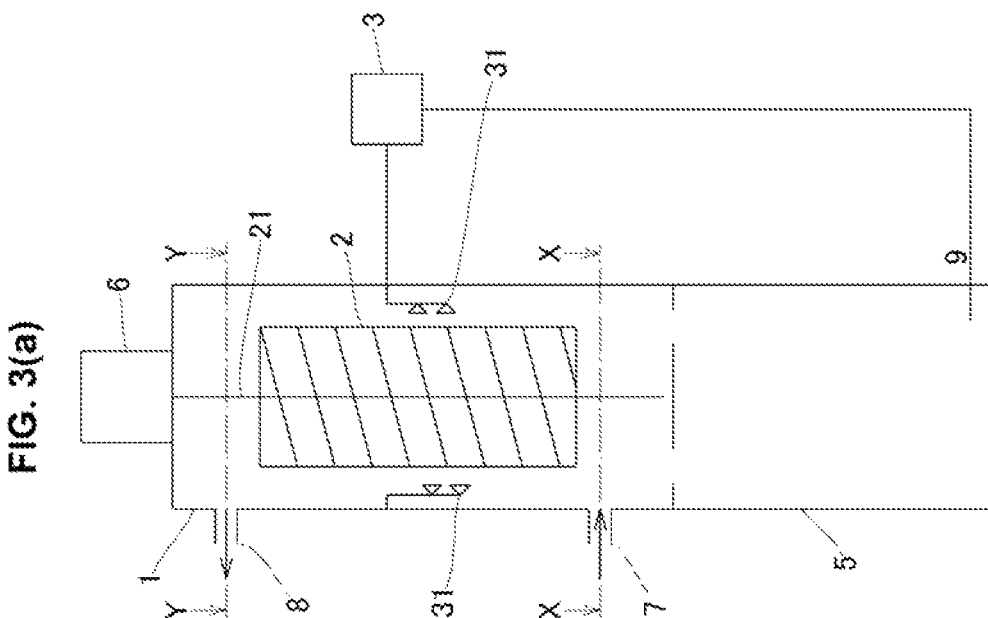

Furthermore, as shown in the second modified example illustrated in FIG. 3, the gas can be introduced from the gas introducing portion 7 to the treatment room 1, and the gas can be discharged from the treatment room 1 via the gas discharging portion 8, by an action of only an airflow generated by the rotation of the catcher 2 formed of the rotary brush.

Airflow guide plates 11 and 12 are formed in the treatment room 1 forming the gas introducing portion 7 and the gas discharging portion 8 so that an atmospheric pressure difference due to an airflow generated by the rotation of the catcher 2 formed of a rotary brush, whereby the gas is introduced from the gas introducing portion 7 to the treatment room 1, and the gas is discharged from the treatment room 1 via the gas discharging portion 8.

In this case, as the catcher 2 formed of a rotary brush, a disk brush, a brush on which the hair 22 is planted by dispersing over almost overall the support 2, etc. can be used besides a spiral brush (the present example). In the case of a spiral brush, the flow amount (treatment amount) of the gas can be increased by allowing the flow direction of the gas of the treatment room 1 (the direction from the bottom to the top) to be coincident with the feed direction of the spiral brush by the rotation direction of the catcher 2 formed of a rotary brush.

Figure 4C:
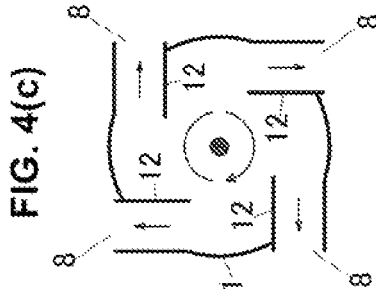
FIGS. 4 (*a*)-4 (*c*) are explanatory drawings illustrating the third modified example of the virus removal device of the present invention, in which FIG. 4 (*a*) is an overall elevational view, FIG. 4 (*b*) is an X-X cross-sectional view of FIG. 4 (*a*), and FIG. 3 (*c*) is a Y-Y cross-sectional view of FIG. 3 (*a*).
Figure 4B:
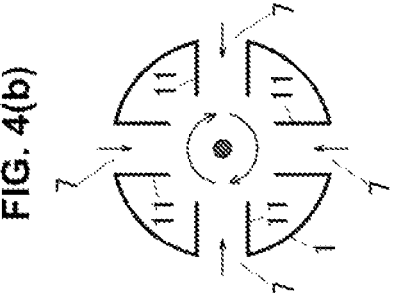
Figure 4A:
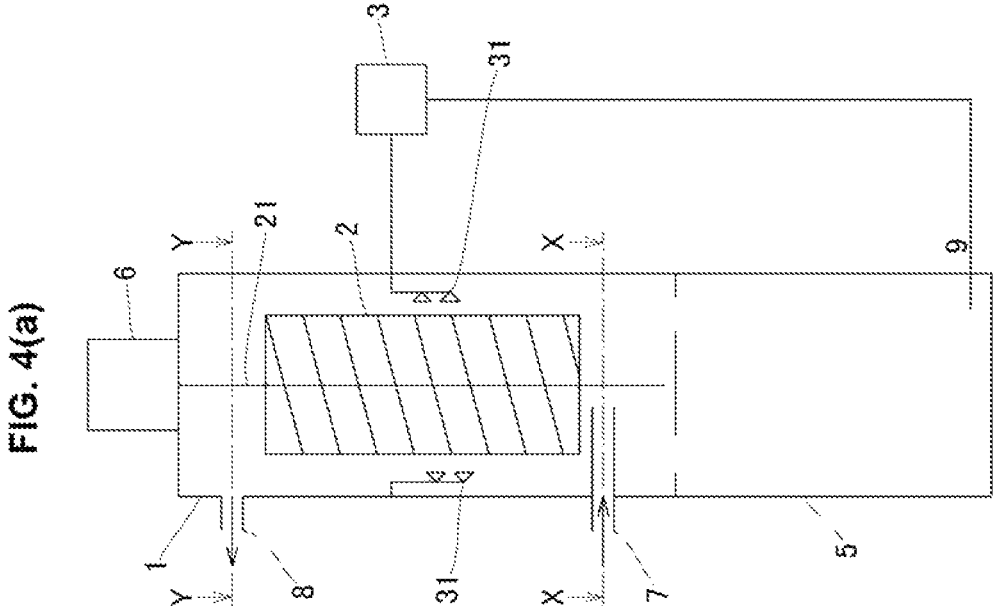

Here, it is possible to allow the gas to be introduced from the gas introducing portion 7 to the treatment room 1 and the gas to be discharged from the treatment room 1 via the gas discharging portion 8, by forming an aperture on the side of the treatment room 1 of the gas introducing portion 7 on the center part of the treatment room 1, in which the air pressure becomes low by an action of an airflow generated by the rotation of the catcher 2 formed of a rotary brush, instead of the airflow guide plate 11, as shown in the third modified example illustrated in FIG. 4; by forming an aperture 7A on the side of the treatment room 1 of the gas introducing portion 7 toward a direction to which a dynamic pressure of an airflow (the arrow in FIG. 5 (*h*)) generated by the rotation of a catcher formed of a rotary brush (illustration is omitted) does not act, as shown in the fourth modified example illustrated in FIG. 5; or by forming an aperture 8A on the side of the treatment room 1 of the gas discharging portion 8 toward a direction to which a dynamic pressure of an airflow (the arrow in FIG. 5 (*d*)) generated by the rotation of a catcher formed of a rotary brush (illustration is omitted) acts, instead of the airflow guide plate 12, as shown in the fourth modified example illustrated in FIG. 5.

Furthermore, the gas discharging portion 8 can be formed into an elbow shape, as shown in the fourth modified example illustrated in FIG. 5, so that the gas is discharged toward the upper side from the treatment room 1 via the gas discharging portion 8.

Incidentally, the constitution can be appropriately modified by forming the gas introducing portion 7 on the upper part (or upper surface) of the treatment room 1 and by forming the gas discharging portion 8 on the bottom of the treatment room 1, or by disposing the axis of the treatment room 1 and catcher 2 (rotary brush) in the horizontal direction or oblique direction other than the perpendicular direction, etc. (illustration is omitted in either case).

By this way, the virus removal device that has been independently installed can be constituted to act by only the driving force of the rotary driving mechanism 6 that rotates the catcher 2 (and the stirrer 4 that can be installed as necessary), whereby the device constitution can be made simple, and a balance between the flow amount (treatment amount) of the gas and the virus remove ability can be easily achieved as compared to the case of that the fan 10 for flowing the gas is installed.

This virus removal device can carry out a treatment of the virus-contained gas smoothly under a low load environment with a small pressure loss, without using a large amount of liquid, at maintenance-free, by washing off the virus collected by the catcher 2 with the liquid sprayed from the spray mechanism 3, once collecting the virus in the liquid storage portion 5 equipped with the stirrer 4 formed on the bottom of the treatment room 1, and sequentially discharging the liquid containing the virus from the liquid storage portion 5 via the liquid discharging portion 9. Specifically, the device can be miniaturized with respect to the amount of air to be treated.

Furthermore, by using a drug liquid that kills the virus for the liquid to be sprayed from the spray mechanism 3, besides the removal of the virus included in the gas, the virus that has been removed from the gas included in the liquid can be killed.

Furthermore, it was confirmed by a performance test that this virus removal device was able to collect particles with a wide range of sizes, specifically at least the particles contained in the gas, and to remove the particles from said gas (the removal rate of particles having a particle size of 0.04 μm: 89%, the removal rate of particles having a particle size of 0.1 μm: 95%). It can be said from this fact that the device exerts an excellent removal performance against viruses (the sizes of coronaviruses: about 0.1 μm).

The virus removal device of the present invention has been explained above based on a plurality of examples. However, the present invention is not limited to the constitutions described in the above-mentioned examples, and the constitution thereof can be appropriately modified within a scope in which the invention does not deviate from the purport thereof, by appropriately combining the constitutions described in the respective examples, or by generally operating by a dry system with a small pressure loss, and carrying out washing with the liquid sprayed from the spray mechanism 3 as necessary, etc.

INDUSTRIAL APPLICABILITY

The virus removal device of the present invention has a property that the device can achieve a high virus removal probability, gives a small pressure loss of the flowed gas, and can miniaturize the device with respect to an amount of air to be treated, by adopting a wet mechanism for removing a virus from a gas. Accordingly, the device can be widely used for use in virus removal devices.

REFERENCE SIGNS LIST 1 treatment room
11 airflow guide plate
12 airflow guide plate 2 catcher (brush)
21 support
22 hair
3 liquid spraying mechanism
31 nozzle
32 pump
4 stirrer
5 liquid storage portion
6 rotary driving mechanism
7 gas introducing portion
8 gas discharging portion
9 liquid discharging portion
10 fan

The invention claimed is:

1. A virus removal device having a function to remove a virus from a gas, comprising:
   a cylindrical treatment room configured to introduce a gas and remove a virus from the gas;
   a catcher formed of a rotary brush, which is installed in the treatment room and configured to collect the virus contained in the gas;
   a liquid spraying mechanism installed in the treatment room;
   a rotary driving mechanism configured to rotate the catcher;
   a gas introducing portion configured to introduce the gas to the treatment room;
   a gas discharging portion configured to discharge the gas from which the virus has been removed from the treatment room; and
   a liquid discharging portion configured to discharge a liquid containing the virus that has been removed from the gas,
   wherein the gas is introduced from the gas introducing portion to the treatment room and the gas is discharged from the treatment room through the gas discharging portion by an action of only an airflow generated by rotation of the catcher formed of the rotary brush,
   wherein the gas introducing portion includes a first aperture formed on a first side of the treatment room, the first aperture being arranged so as to face away from the airflow such that the airflow flows along side the first aperture, and
   wherein the gas discharging portion includes a second aperture formed on a second side of the treatment room, the second aperture being arranged to face the airflow in an oncoming direction of the airflow such that the airflow is discharged through the second aperture of the gas discharging portion.

2. The virus removal device according to claim 1, wherein the liquid spraying mechanism is installed in an intermediate position of the treatment room, and first and second portions of the catcher formed of the rotary brush are disposed on top and bottom sides of the liquid spraying mechanism, respectively.

3. The virus removal device according to claim 1, wherein the virus removal device is configured to circulate the liquid that has been discharged from the liquid discharging portion into the liquid spraying mechanism.

4. The virus removal device according to claim 1, wherein the liquid contains a component that kills the virus.

5. The virus removal device according to claim 1, further comprising a light source configured to irradiate the liquid with a light that kills the virus.

* * * * *